(12) United States Patent
Kitagawa et al.

(10) Patent No.: US 7,852,102 B2
(45) Date of Patent: Dec. 14, 2010

(54) METHOD AND APPARATUS FOR INSPECTING SEMICONDUCTOR DEVICE

(75) Inventors: Hiroki Kitagawa, Kadoma (JP); Hiroaki Katsura, Kadoma (JP)

(73) Assignee: Panasonic Corporation, Osaka (JP)

( * ) Notice: Subject to any disclaimer, the term of this patent is extended or adjusted under 35 U.S.C. 154(b) by 288 days.

(21) Appl. No.: 12/294,127

(22) PCT Filed: Feb. 26, 2008

(86) PCT No.: PCT/JP2008/000336

§ 371 (c)(1),
(2), (4) Date: Sep. 23, 2008

(87) PCT Pub. No.: WO2008/129755

PCT Pub. Date: Oct. 30, 2008

(65) Prior Publication Data

US 2010/0231253 A1      Sep. 16, 2010

(30) Foreign Application Priority Data

Apr. 10, 2007   (JP) .............................. 2007-102598

(51) Int. Cl.
*G01R 31/26*   (2006.01)

(52) U.S. Cl. ..................................... 324/765; 324/751

(58) Field of Classification Search ...................... None
See application file for complete search history.

(56) References Cited

U.S. PATENT DOCUMENTS

| 5,708,371 A * | 1/1998 | Koyama .................... 324/752 |
| 2006/0006886 A1 | 1/2006 | Yamashita et al. .......... 324/751 |
| 2007/0018634 A1 | 1/2007 | Ohtake et al. ................ 324/96 |
| 2007/0035726 A1 | 2/2007 | Takahashi et al. ......... 356/237.1 |

FOREIGN PATENT DOCUMENTS

JP      2006-270063      10/2006

* cited by examiner

*Primary Examiner*—Minh N Tang
(74) *Attorney, Agent, or Firm*—Steptoe & Johnson LLP

(57) ABSTRACT

The magnitude of an amplitude waveform of an electromagnetic wave generated when irradiating a pulse laser beam to a structure A including diffusion regions provided in the structure of a semiconductor device to be inspected is compared with the magnitude of an amplitude waveform of an electromagnetic wave radiated when irradiating the pulse laser beam to a structure A of a reference device measured in advance, and the detection sensitivity of the electromagnetic wave is corrected (S14). Thereafter, measurement errors caused by variations in the detection sensitivity of electromagnetic waves of an inspecting apparatus are eliminated by inspecting the semiconductor device as an inspection target, so that the quality of the semiconductor device is precisely determined (S16).

4 Claims, 16 Drawing Sheets

(a)

(b)

(c)

(a)

(b)

ly known non-contact inspection method is performed by irradiating a pulse laser beam 110 to a P-type diffusion region 101, an N-type diffusion region 102, constituting an MOS transistor or the like, or a built-in electric field generation portion such as a metal semiconductor interface which is disposed in a semiconductor device provided on a stage 108 to detect an electromagnetic wave radiated toward free space. Reference Numeral 103 denotes a board. Reference Numeral 104 denotes an insulating film. Reference Numerals 105, 106, and 107 denote wiring lines.

METHOD AND APPARATUS FOR INSPECTING SEMICONDUCTOR DEVICE

The present application is based on International Application PCT/JP2008/000336 filed Feb. 26, 2008, which claims priority to Japanese Patent Application No. 2007-102598, filed Apr. 10, 2007, the entire contents of which are hereby incorporated by reference.

TECHNICAL FIELD

The present invention relates to a method and an apparatus for inspecting a semiconductor device to examine the quality of a semiconductor device by detecting a defect such as a broken wiring line in the semiconductor device, the inspected semiconductor device being provided with an electronic circuit on a board.

BACKGROUND ART

Multiple electronic circuits are formed in a semiconductor device mounted in an electronic element. As a non-contact inspection method of inspecting a broken wiring line or the like occurring during the manufacture of the electronic circuits in a non-contact manner, there is a known method, which is disclosed in Patent Document 1, for example, of inspecting a defective PN junction, a broken wiring line, a short-circuit, or a high resistant portion.

As shown in FIG. 13, the known non-contact inspection method is performed by irradiating a pulse laser beam 110 to a P-type diffusion region 101, an N-type diffusion region 102, constituting an MOS transistor or the like, or a built-in electric field generation portion such as a metal semiconductor interface which is disposed in a semiconductor device provided on a stage 108 to detect an electromagnetic wave radiated toward free space. Reference Numeral 103 denotes a board. Reference Numeral 104 denotes an insulating film. Reference Numerals 105, 106, and 107 denote wiring lines.

A defect diagnosis of the semiconductor device is performed by detecting the electromagnetic wave radiated from the pulse laser irradiated position in this way, converting the detected electromagnetic wave into a time-varying voltage signal corresponding to a time waveform of an electric field amplitude of the electromagnetic wave, and detecting electric filed distribution in the semiconductor device.

Specifically, in a step S1 shown in FIG. 14, an amplitude waveform of an electromagnetic wave radiated toward free space is acquired by irradiating a pulse laser beam to a predetermined inspection region of an inspection target.

In a step S2, a quality determination is made by comparing the amplitude waveform of the electromagnetic wave acquired in the step S1 with an amplitude waveform which has been measured and acquired in advance and radiated from the predetermined inspection region in a non-defective device.

FIG. 15 shows an amplitude waveform of an electromagnetic wave generated when irradiating a pulse laser beam to a semiconductor circuit. On the assumption that the amplitude waveform shown in FIG. 15 is an amplitude waveform of an electromagnetic wave generated from a predetermined inspection position in a non-defective device, the quality of a semiconductor device is determined by comparing a maximum value V of the amplitude waveform of the electromagnetic wave at time T, for example, with the maximum value of an amplitude waveform generated from the predetermined inspection region of the semiconductor device as an inspection target.

A criterion for the quality determination varies with inspection items. Since the maximum value or the minimum value of an amplitude waveform of an electromagnetic wave varies with a difference in the structure of a pulse laser beam irradiated position in many cases, the maximum value or the minimum value of the amplitude waveform of the electromagnetic wave is compared. When the maximum value or the minimum value is different from that of a reference device, it is determined that a semiconductor device having the value as an inspection target has a defect.

Patent Document 1: JP-A-2006-24774

DISCLOSURE OF THE INVENTION

Problem That the Invention is to Solve

However, the known configuration has a problem in that the amplitude magnitude of an electromagnetic wave to be detected becomes considerably weak when a semiconductor device as an inspection target is replaced, an angle for irradiating a laser beam to a semiconductor device is changed, or an electromagnetic wave detector is replaced.

For example, relative to the configuration of the semiconductor device which generates the amplitude waveform of the electromagnetic wave shown in FIG. 15, when the semiconductor device shown in FIG. 13 is detached from the stage 108 and installed again to measure the same portion, an amplitude waveform of an electromagnetic wave shown in FIG. 16 may be detected due to some factors such as sensitivity change of control equipment or angle change of laser irradiation to the semiconductor device.

However, when sensitivity is corrected by readjusting an optical component or a control device included in an inspection apparatus, the same amplitude waveform of an electromagnetic wave as that in FIG. 15 can be acquired.

Thus, when the amplitude magnitude of an electromagnetic wave obtained by measurement in an inspection region is simply compared with that of a non-defective device, there is a possibility that an originally non-defective portion is erroneously determined to be defective due to a difference in the amplitude magnitude of an electromagnetic wave caused when the inspection apparatus is not sufficiently corrected.

In order to correct the sensitivity of the inspection apparatus, a target which surely generates a stable amplitude waveform of an electromagnetic wave when irradiating a pulse laser beam, that is, a reference measurement device is necessary. However, the magnitude of the amplitude of an electromagnetic wave radiated from crystal of InAs or the like which meets the condition is 10 or more times as large as the magnitude of the amplitude of an electromagnetic wave generated from a semiconductor device having a widely used silicon board. Moreover, even though such material is used to correct the sensitivity, there is a possibility that the sensitivity may not be corrected precisely to detect the amplitude waveform of an electromagnetic wave generated from the semiconductor device.

The invention is devised to solve the above-described problems of the known technique, and an object of the invention is to provide a method and an apparatus for inspecting a semiconductor device, which are capable of preventing an erroneous determination of the quality of a semiconductor device caused due to a comparison error of the amplitude magnitude of an electromagnetic wave when a pulse laser beam is irradiated to the semiconductor device.

Means for Solving the Problem

Aspect 1 of the present invention provides a method of inspecting a semiconductor device including: an irradiation step of irradiating a pulse laser beam to any diffusion region in a semiconductor device as an inspection target, the semiconductor device being held in an non-bias state and including diffusion regions; a detection and conversion step of detecting an electromagnetic wave radiated from a laser beam irradiated position of the semiconductor device, and converting the detected electromagnetic wave into a time-varying voltage signal corresponding to a time waveform of an electric field amplitude of the electromagnetic wave; and a defect diagnosis step of detecting electric field distribution within the semiconductor device from the time-varying voltage signal to perform a defect diagnosis. The method further includes: comparing a first time waveform of the electric field amplitude of the electromagnetic wave generated when irradiating the pulse laser beam to the diffusion region for correcting the detection sensitivity of the electromagnetic wave which is provided in the semiconductor device as an inspection target and connected to at least one wiring line with a second time waveform of the electric field amplitude of the electromagnetic wave generated when irradiating the pulse laser beam to the diffusion region for correcting which is provided in a semiconductor device as a reference device; correcting the detection sensitivity of the electromagnetic wave so that the maximum value of the amplitude magnitude of the electromagnetic wave for the first time waveform is equal to the maximum value of the amplitude magnitude of the electromagnetic wave for the second time waveform; and inspecting the semiconductor device as an inspection target. With such a method, it is possible to perform an inspection while avoiding the influence of a magnitude difference in the amplitude waveform of an electromagnetic wave caused due to an angle change of laser irradiation to a semiconductor device as an inspection target or correction error of a control device included in an apparatus.

Aspect 2 or 3 of the present invention provides the method of inspecting a semiconductor device described in Aspect 1, wherein the diffusion region for correcting the detection sensitivity of the electromagnetic wave is not electrically connected to the plurality of diffusion regions included in the semiconductor device, and wherein the correction of the detection sensitivity of the electromagnetic wave is performed so that values of the amplitude magnitudes of the electromagnetic waves at a specific time are equal to each other in amplitude waveforms of the electromagnetic waves of the first time waveform and the second time waveform, instead of performing the correction using the maximum value of the amplitude magnitude of the electromagnetic wave. With such a method, it is possible to easily radiate the electromagnetic wave. Even when the electromagnetic wave radiated from the semiconductor device as an inspection target has a plurality of extreme values and the correction is not sufficiently made just by adjusting the maximum value, the sensitivity can be corrected.

Aspect 4 of the present invention provides a semiconductor device inspecting apparatus including: an irradiation unit which two-dimensionally irradiates a pulse laser beam having a predetermined wavelength to a semiconductor device held in a non-bias state; a detection and conversion unit which detects an electromagnetic wave radiated from the laser beam irradiated position of the semiconductor device and converts the detected electromagnetic wave into a time-varying voltage signal corresponding to a time waveform of the electric field amplitude of the electromagnetic wave; a defect diagnosis unit which detects electric field distribution within the semiconductor device from the time-varying voltage signal to perform a defect diagnosis; and a semiconductor device for correcting the sensitivity of the electromagnetic wave which is arranged within a range where the irradiation unit irradiate the pulse laser beam. The detection sensitivity of the electromagnetic wave generated when irradiating the pulse laser beam to the semiconductor device for correcting the sensitivity of the electromagnetic wave before component replacement is equal to the detection sensitivity of the electromagnetic wave generated after component replacement. With such a configuration, it is possible to perform sensitivity correction for acquiring the amplitude waveform of an electromagnetic wave even when replacing the component is replaced, thereby inspecting a semiconductor device with high precision.

Advantage of the Invention

According to the present invention, there is provided an advantage of improving inspection precision in that a quality of a semiconductor device as an inspection target can be determined precisely, avoiding the influence of a difference in measurement results caused due to insufficient sensitivity correction when an amplitude magnitude is acquired from the amplitude waveform of an electromagnetic wave.

BRIEF DESCRIPTION OF THE DRAWINGS

FIG. 5A shows the amplitude waveform of the electromagnetic wave generated from a reference device. FIG. 5B shows the amplitude waveform of the electromagnetic wave generated from a semiconductor device as an inspection target. FIG. 5C shows the amplitude waveform of the electromagnetic wave generated from the semiconductor device as an inspection target after correction of sensitivity.

FIG. 6A shows the amplitude waveform of the electromagnetic wave generated from the reference device and FIG. 6B shows the amplitude waveform of the electromagnetic wave generated from the semiconductor device as an inspection target.

FIG. 12A shows the amplitude waveform of the electromagnetic wave generated from an electromagnetic wave detector 1006. FIG. 5B shows the amplitude waveform of the electromagnetic wave generated from an electromagnetic wave detector 2006. FIG. 5C shows the amplitude waveform of the electromagnetic wave generated from the electromagnetic wave detector 2006 after correction of sensitivity.

BEST MODE FOR CARRYING OUT THE INVENTION

Hereinafter, exemplary embodiments of the invention will be described with reference to the drawings.

First Embodiment

Figure 1:
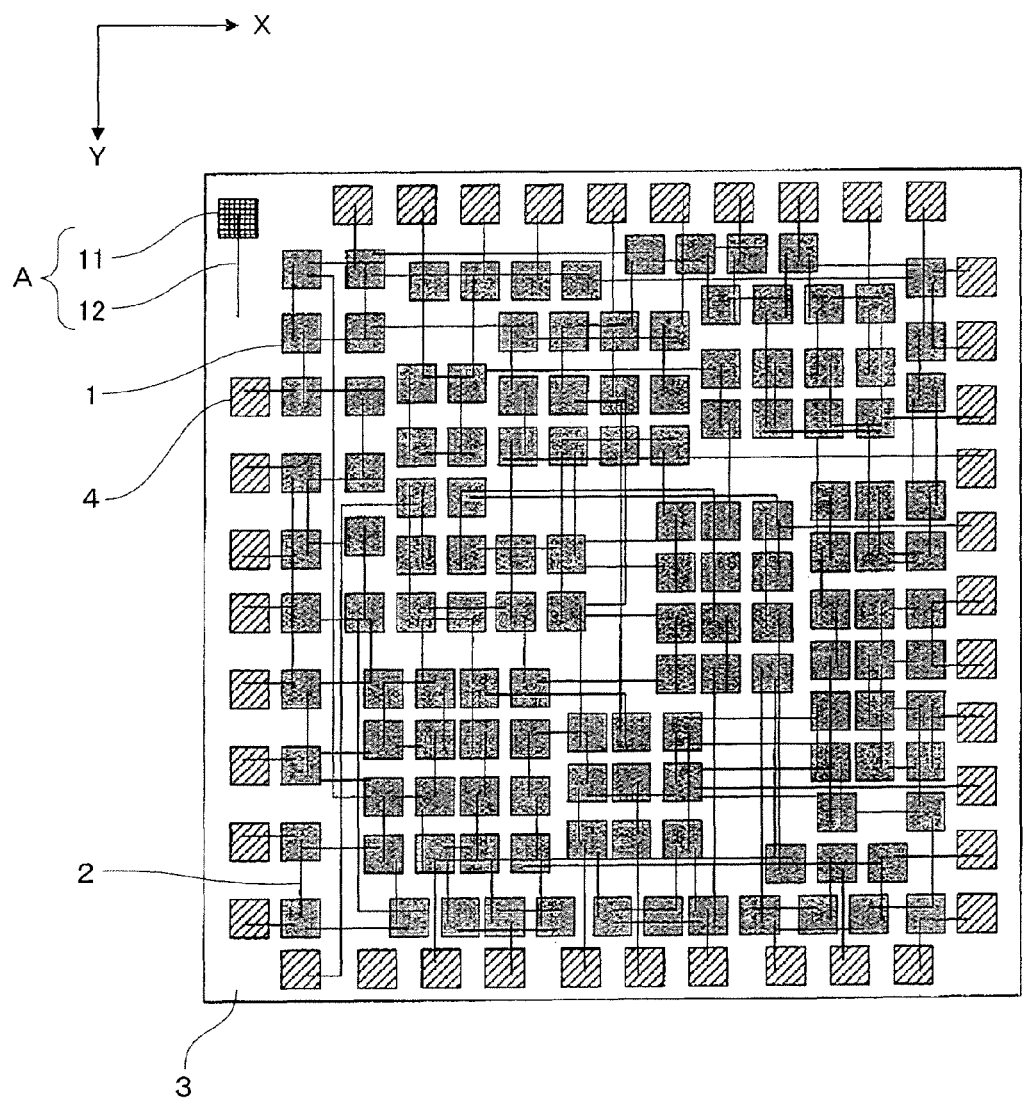
FIG. 1 is a diagram illustrating a circuit configuration of a semiconductor device according to a first embodiment of the invention.

FIG. 1 shows a semiconductor device having a structure as an inspection target according to the invention and is a conceptual plan view illustrating the arrangement of electronic circuits constituted by diffusion regions and wiring lines.

In FIG. 1, a plurality of diffusion regions 1 and a plurality of wiring lines 2 are included in the semiconductor device. Accordingly, the same reference numerals are given to constituent elements which do not have an effect on the invention and the description will be made.

In order to fulfill functions required for the semiconductor device, the p-type or n-type diffusion regions (hereinafter, simply referred to as diffusion regions) 1 are arranged innumerably on a board 3 and corrected through the wiring lines 2. In addition, some of the diffusion regions 1 are connected to electrode pads 4 arranged on the board 3 to transmit and receive an electric signal.

Since the semiconductor device realizes the required functions by transmitting and receiving an electric signal via the diffusion regions 1 to and from another electronic device using the electrode pads 4, the wiring line 2 connected to the diffusion region 1 is generally connected to another diffusion region 1 or one electrode pad 4 arranged on the board 3.

As shown in FIG. 1, the semiconductor device as an inspection target according to the invention has a structure (hereinafter, referred to as a structure A) which includes a diffusion region 11 formed separately from the above-described circuit configuration and at least one wiring line 12 connected to the diffusion region 11.

Next, in order to describe a specific structure by which the invention is characterized and in which an electromagnetic wave is likely to be generated when irradiating a pulse laser beam, the principle of generating the electromagnetic wave by irradiating the pulse laser beam will be simply described.

A built-in electric field is generated in the diffusion region included in the semiconductor device and constituting an MOS transistor circuit or the like, a metal/semiconductor interface, or the like. Thus, when the pulse laser beam having a predetermined pulse width (for example, in a case where the semiconductor device is a silicon board, an electromagnetic wave is easily generated when the pulse laser beam having a pulse width of between 1 femtosecond or more and 10 picosecond or less is irradiated to the diffusion region) is irradiated to the diffusion region, pairs of an electron and a hole are instantly formed, thereby radiating the electromagnetic wave.

The experiment carried out by the inventors shows that a waveform having a strong amplitude of an electromagnetic wave is detected when the pulse laser beam is irradiated to the diffusion region connected to the wiring line. However, in a case where the wiring line is not joined to the diffusion region, an electromagnetic wave cannot be detected since the electromagnetic wave is radiated weakly or the electromagnetic wave is not radiated.

In a case where the diffusion region 1 shown in FIG. 1 is connected to another diffusion region 1 through the wiring line 2, it is not easy to detect or predict the amplitude waveform of an electromagnetic wave generated in the diffusion region 1 and the wiring line 2 connected to each other since the amplitude waveform of the radiated electromagnetic wave is influenced.

There is a material such as InAs which easily radiates an electromagnetic wave having a strong amplitude when irradiating a pulse laser beam. However, embedding single crystal of such a material in the widely used semiconductor device including a silicon board is highly disadvantageous in terms of a manufacturing method and cost.

Thus, the invention is devised to provide a method of correcting the amplitude magnitude of the electromagnetic wave using the electromagnetic wave radiated when irradiating the pulse laser beam to the diffusion region (the structure A) provided in the semiconductor device and connected to at least one wiring line; and then inspecting the semiconductor device.

Figure 2:
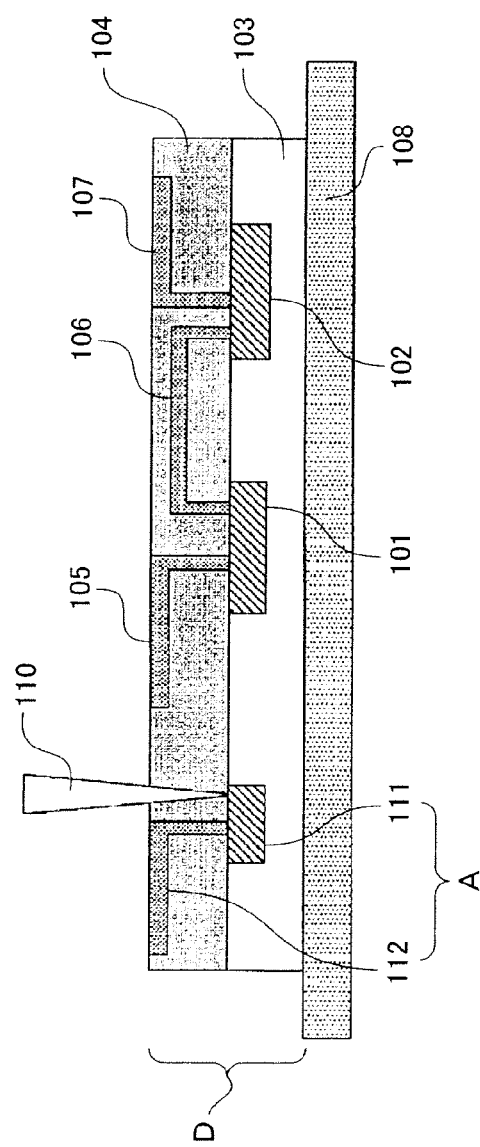
FIG. 2 is a sectional view illustrating the configuration of the semiconductor device according to the first embodiment.

A configuration example of the semiconductor device for performing the inspection is shown in FIG. 2.

Figure 13:
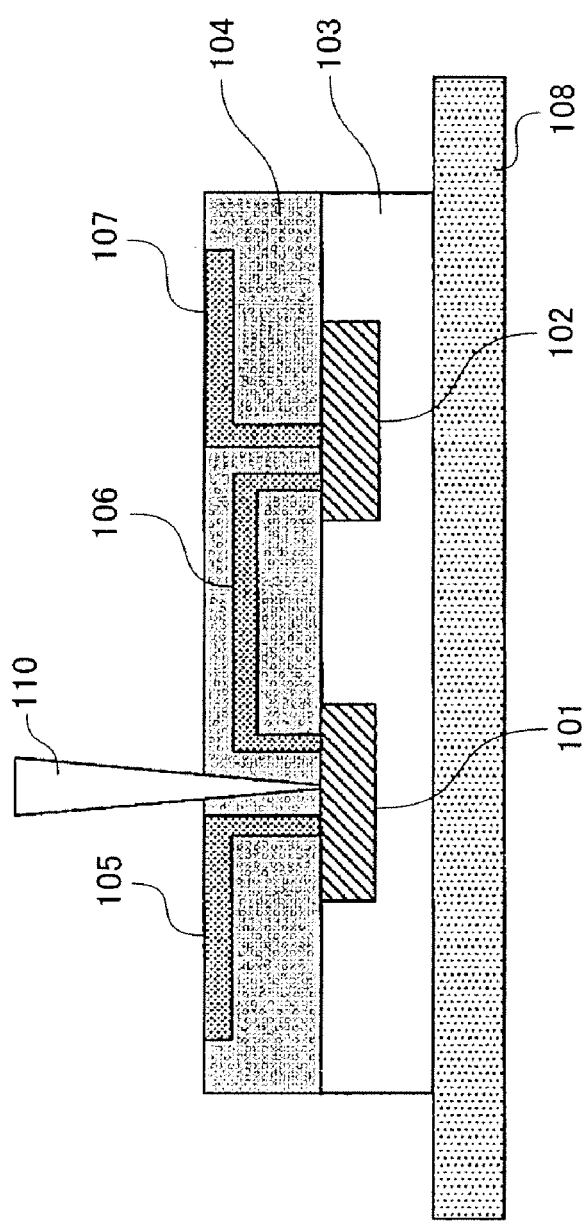
FIG. 13 is a sectional view illustrating the configuration of a conventional semiconductor device.
Figure 14:
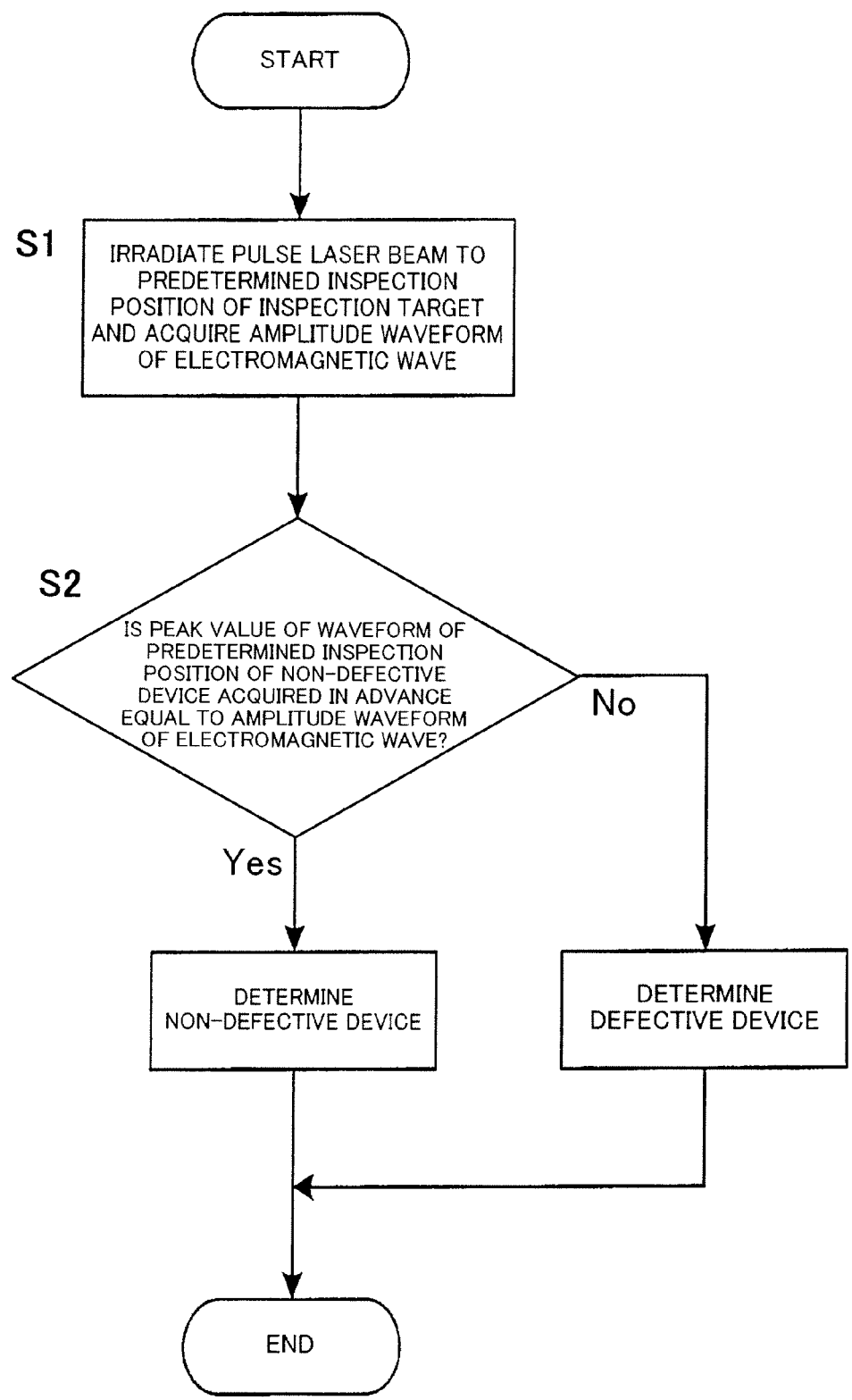
FIG. 14 is a flowchart illustrating a conventional non-contact inspecting method

FIG. 2 is a sectional view of the semiconductor device as an inspection target. In this case, in FIG. 2, the same reference numerals are given to constituent elements having the functions corresponding to those of the constituent elements described in FIG. 13 in which a known example is shown. The description thereof is omitted.

A structure A does not function as an electronic circuit alone, since a wiring line 112 connected to a diffusion region 111 of the semiconductor device structure used in the invention is not connected to diffusion regions 101 and 102 included in a board 103, and the structure A (which includes the diffusion region 11 and the wiring line 12 in FIG. 1) including the diffusion region 111 and the wiring line 112 is formed separately from a circuit configuration (the diffusion region 1 or the electrode pad 4 in FIG. 1) having a different function and cannot transmit and receive an electric signal to and from an external electric circuit. For this reason, such a structure A is not included in a general semiconductor device.

Figure 15:
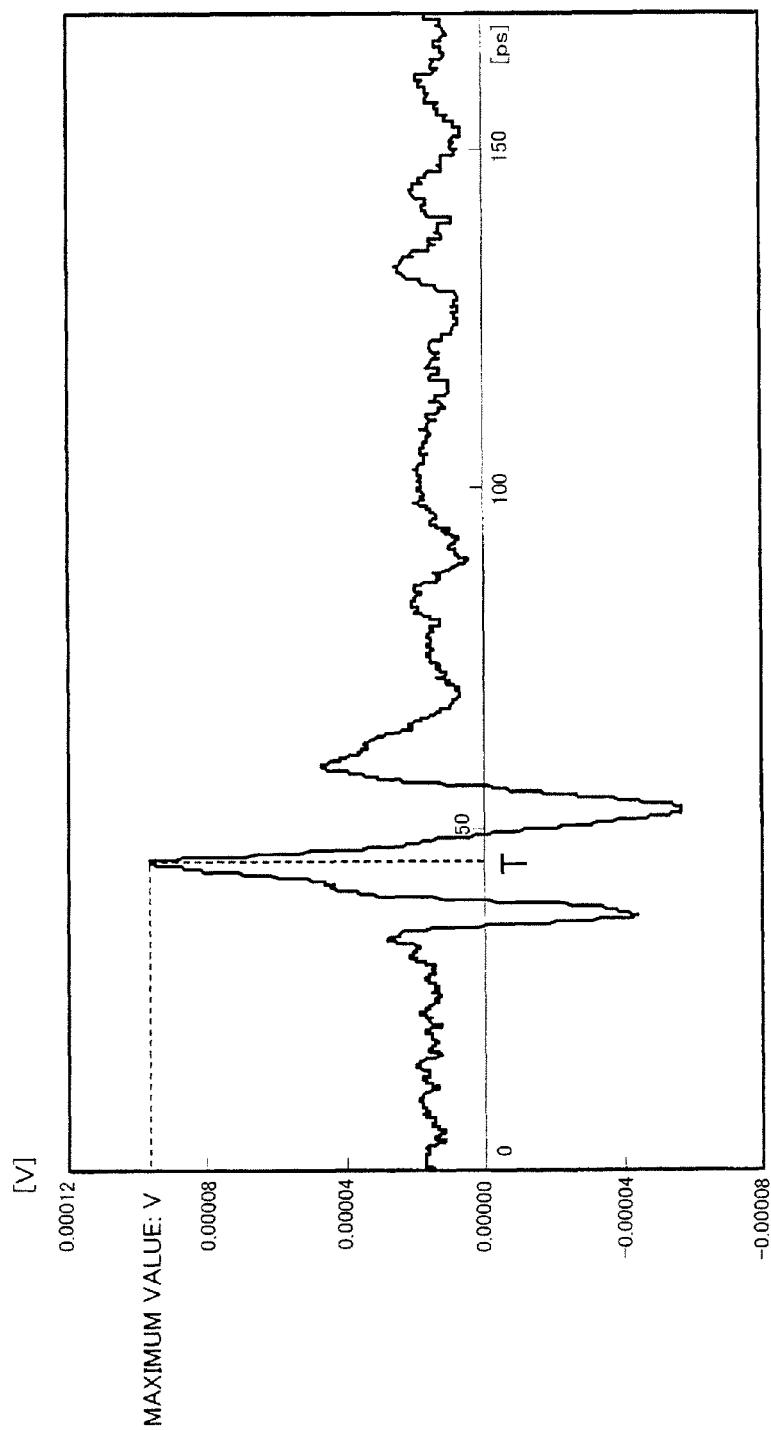
FIG. 15 is a diagram illustrating an amplitude waveform of an electromagnetic wave generated by irradiating the pulse laser beam to the semiconductor device.
Figure 16:
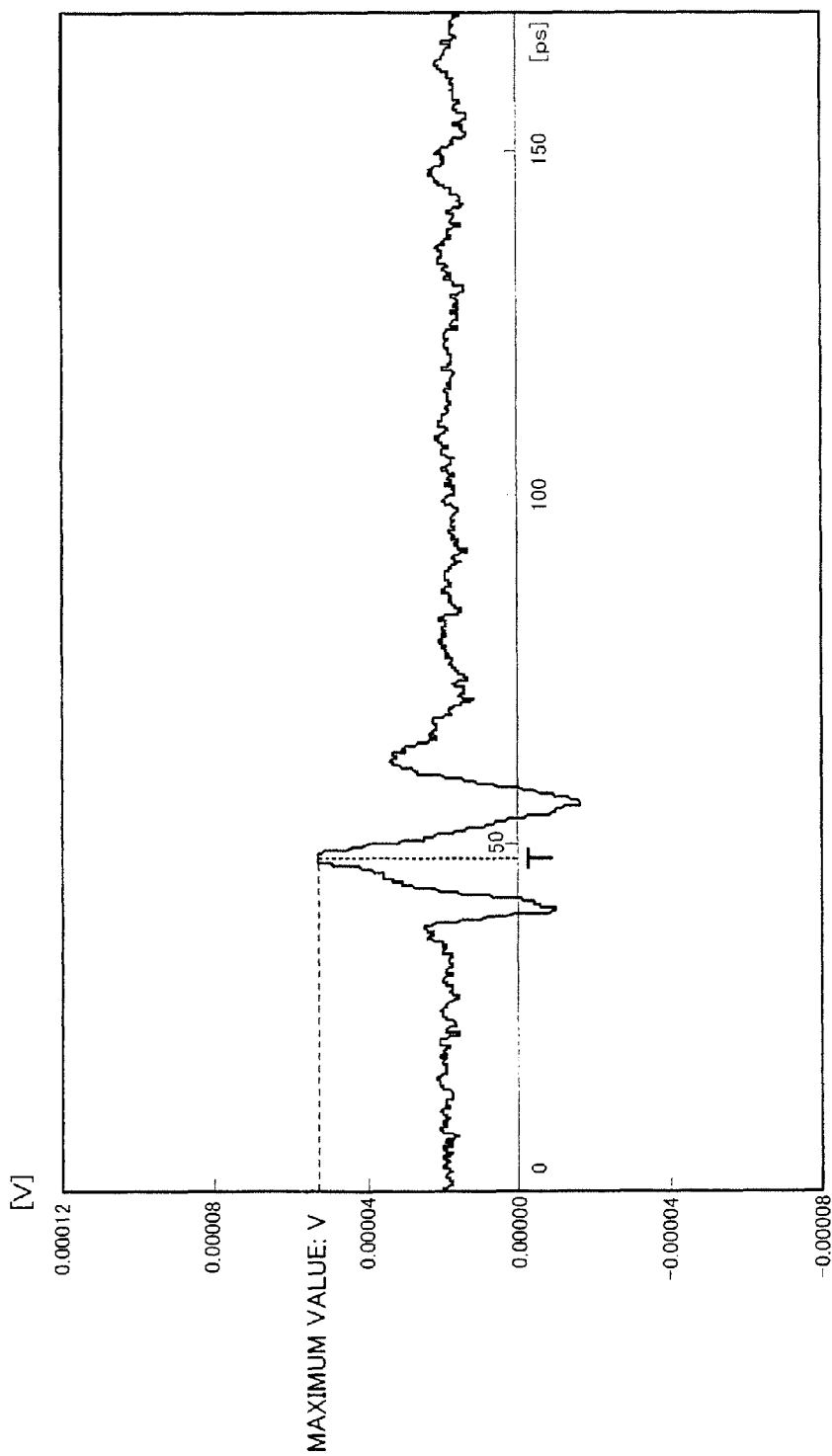
FIG. 16 is a diagram illustrating an amplitude waveform of an electromagnetic wave generated due to sensitivity shortage when irradiating the pulse laser beam to the semiconductor device.

As for the plane arrangement of the structure A, it is preferable that the wiring line 12 linearly extends from the diffusion region 11 like the diffusion region 11 and the wiring line 12 shown in FIG. 1. That is because the maximum value of the amplitude of the radiated electromagnetic wave is reduced when the wiring line 12 extending from the diffusion region 11 diverges along the way. The optimum length of the wiring line 12 for easily radiating the electromagnetic wave depends on the area of the diffusion region 11 or the magnitude of the irradiated pulse laser beam. By way of example, when the diffusion region 11 is 10 μm squared and the length of the wiring line 12 is 300 μm, the amplitude waveform of the generated electromagnetic wave is a waveform shown in FIG. 15.

The amplitude waveform of the radiated electromagnetic wave is also influenced by the peripheral structure of the arranged structure A. Accordingly, when the pulse laser beam is irradiated to the structure A including the diffusion region 11 which is 10 μm squared and the wiring line 12 of which the length is 300 μm, the amplitude waveform of the electromagnetic wave shown in FIG. 15 cannot be necessarily obtained. However, the electromagnetic wave is easily radiated.

The structure A is used in a non-contact inspection performed to determine the quality of the semiconductor device using the amplitude magnitude of the electromagnetic wave generated when irradiating the pulse laser beam to the semiconductor device, or using electric field distribution in the semiconductor device.

In the non-contact inspection technique, the quality of the semiconductor device can be determined only by irradiating the pulse laser beam since a process of preparing an electronic probe for applying voltage and a process of applying voltage are not necessary, unlike a known electric inspection. If the precision of the quality determination is improved, the non-contact inspection technique performed by irradiating the pulse laser beam is an effective inspection method A configuration example of a non-contact inspecting device for performing the non-contact inspection technique is shown in FIG. 3.

Figure 3:
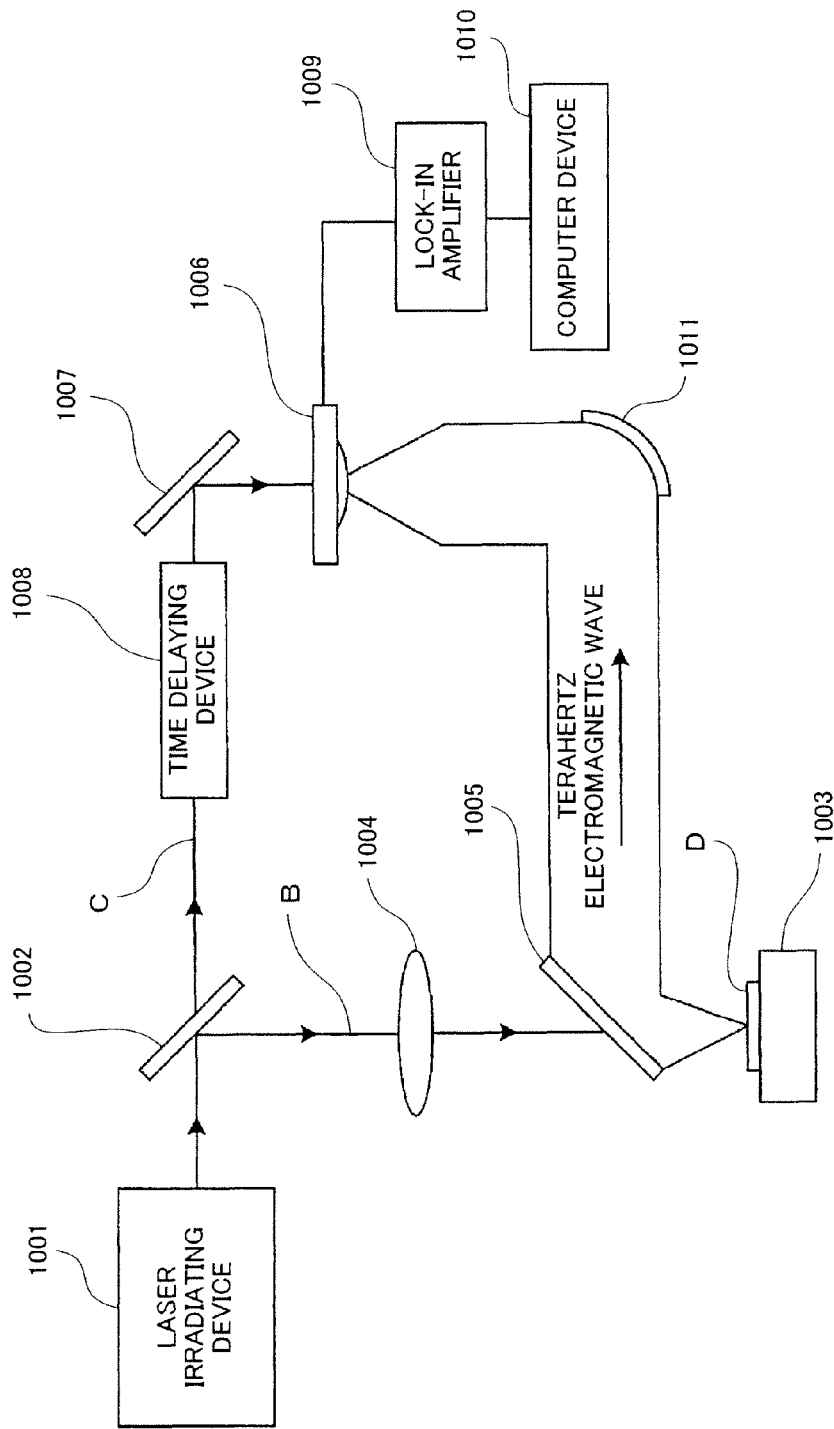
FIG. 3 is a block diagram illustrating an electromagnetic wave detector used in non-contact inspection according to the first embodiment.

The device configuration for realizing the non-contact inspection technique is not limited to the configuration in FIG. 3, but may be modified in various forms without departing from the scope of the non-contact inspection technique performed to detect the electromagnetic wave to be generated by irradiating the laser beam.

As shown in FIG. 3, a pulse laser beam emitted from a laser irradiating device 1001 is split into an inspecting laser beam (hereinafter, referred to as a pump beam) B and a triggering laser beam (hereinafter, referred to as a probe beam) C for driving an electromagnetic detector by a splitter 1002. The pump beam B is irradiated to a semiconductor device D as an inspection target installed on a stage 1003 through a collective lens 1004 and a half-mirror (for example, a mirror having a transparent film (ITO film)) 1005. The semiconductor device D can be moved by the stage 1003 in a horizontal direction. The semiconductor device D is held in a non-bias state during the inspection.

A terahertz electromagnetic wave generated in the semiconductor device D is reflected by the half-mirror 1005 and guided to an electromagnetic wave detector (electromagnetic wave detecting unit) 1006 through a parabolic mirror 1011. In the electromagnetic wave detector 1006, the probe beam C as a trigger beam has been irradiated through a time delaying device (time delaying unit) 1008, which sequentially delays the probe beam C from the splitter 1002, and a reflection mirror 1007.

Only a detection signal (a current signal) having a predetermined frequency detected thus by the electromagnetic detector 1006 is amplified by a lock-in amplifier 1009, and the detected signal amplified by the lock-in amplifier 1009 is input into a computer device 1010. The computer device 1010 functions as a defect detecting unit and a device control unit for determining whether a defect such as a broken wiring line or a short-circuit is present in the semiconductor device D and for performing control process of the inspection device such as operational control of the stage 1003 by analyzing the detected signal amplified by the lock-in amplifier 1009.

The case of inspecting a diffusion region 101 shown in FIG. 2, according to the first embodiment, will be described with reference to FIGS. 3, 4, 5A to 5C, 6A, and 6B.

Figure 4:
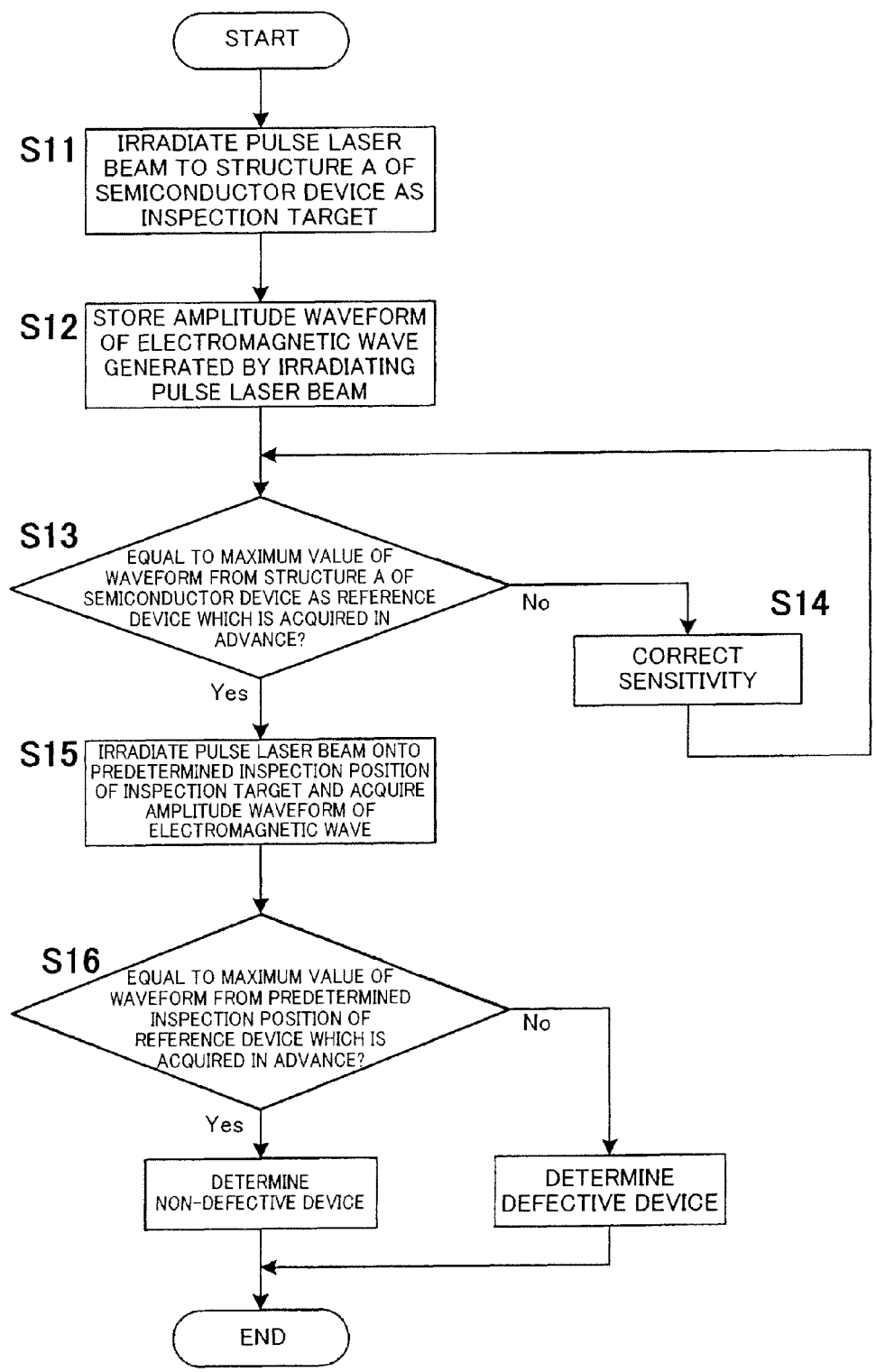
FIG. 4 is a flowchart illustrating a process of the non-contact inspection according to the first embodiment.
Figure 5:
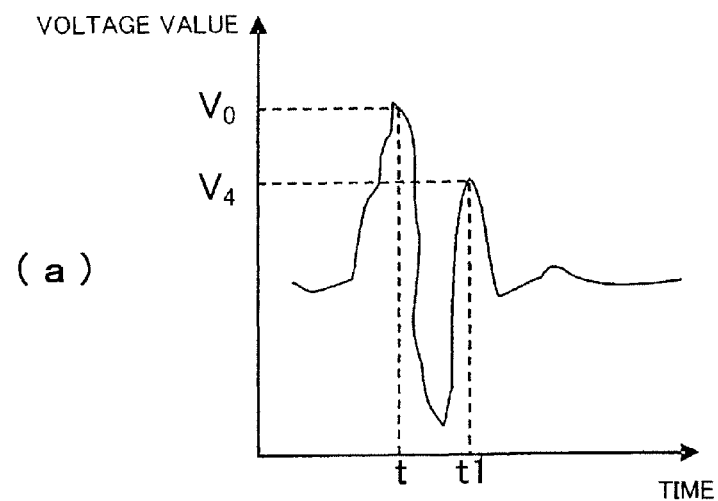
FIGS. 5A to 5C are diagrams illustrating amplitude waveforms of electromagnetic waves when irradiating a pulse laser beam to a structure A according to the first embodiment.
Figure 5:
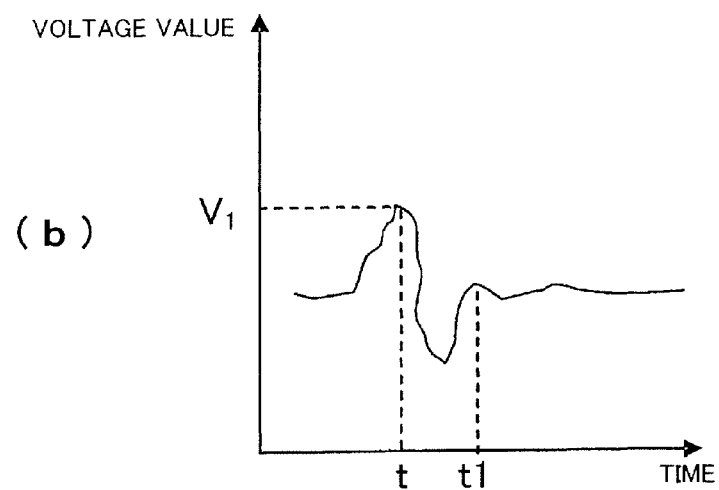
Figure 5:
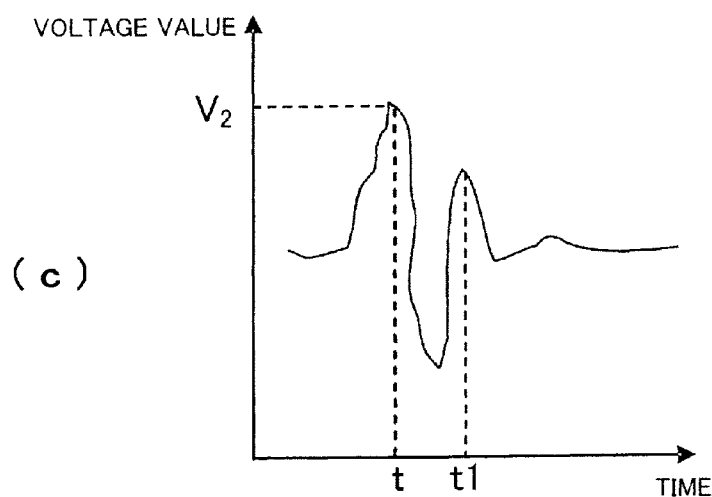

FIG. 4 is a flowchart illustrating an inspection process performed when the semiconductor device having the structure A is inspected by the inspection device shown in FIG. 3. FIGS. 5A to 5C are schematic diagrams illustrating the amplitude waveforms of the electromagnetic wave generated when irradiating the pulse laser beam to the structure A. FIG. 5A shows the amplitude waveform of the electromagnetic wave generated from a reference device. FIG. 5B shows the amplitude waveform of the electromagnetic wave generated from the semiconductor device as an inspection target. FIG. 5C shows the amplitude waveform of the electromagnetic wave generated from the semiconductor device as an inspection target after correction of sensitivity.

Figure 6:
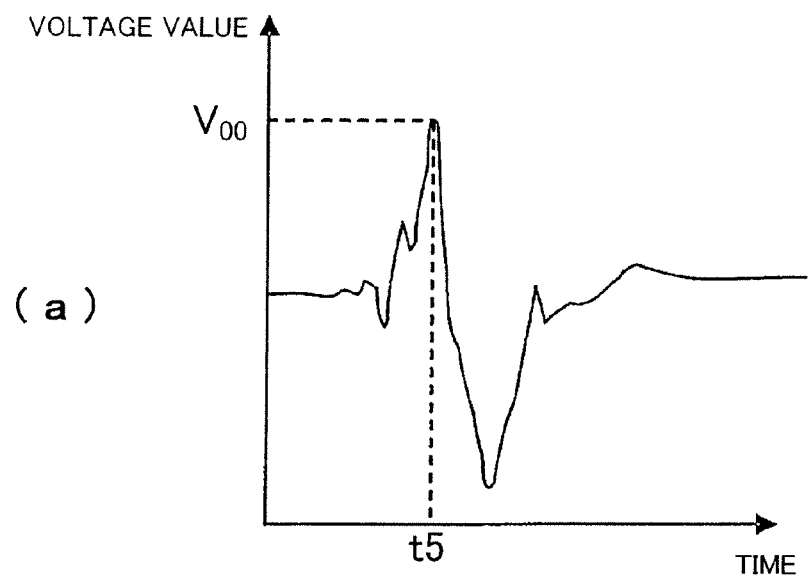
FIGS. 6A and 6B are diagrams illustrating amplitude waveforms of electromagnetic waves generated when irradiating the pulse laser beam to an inspection region according to the first embodiment.
Figure 6:
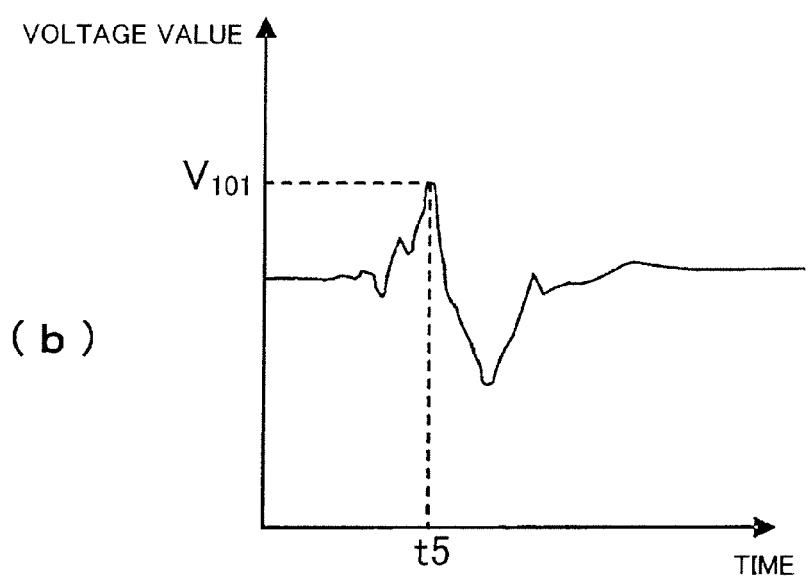

FIGS. 6A and 6B are schematic diagrams illustrating the amplitude waveform of the electromagnetic wave generated when irradiating the pulse laser beam to the diffusion region 101. FIG. 6A shows the amplitude waveform of the electromagnetic wave generated from the reference device and FIG. 6B shows the amplitude waveform of the electromagnetic wave generated from the semiconductor device as an inspection target.

In a step (S11) of irradiating a laser beam in FIG. 4, the semiconductor device D as an inspection target is installed on the stage 108 to irradiate a pulse laser beam 110 to the diffusion region 111 constituting the structure A.

In a step (S12) of recording the amplitude waveform of the electromagnetic wave, the amplitude waveform of the electromagnetic wave generated from the semiconductor device D as an inspection target in the step (S11) of irradiating the laser beam is stored in the computer device 1010.

In a step (S13) of determining whether correction is performed or not, a maximum value V0 of the waveform in FIG. 5A and a maximum value V1 of the waveform in FIG. 5B are compared to each other. When the maximum value V1 is not equal to the maximum value V0, that is, a difference therebetween is equal to or more than a reference value for performing the correction, a step (S14) of correcting sensitivity is performed. Then, the maximum value of the amplitude waveform of the electromagnetic wave shown in FIG. 5C is set to V2 and the step (S14) of correcting the sensitivity is performed again to correct the sensitivity so that a difference between the maximum values V0 and V2 of the amplitude waveform of the electromagnetic wave is equal to or less than the reference value.

A correction unit is not particularly limited. However, when the angle of the probe beam C incident on the electromagnetic wave detector 1006 or the angle of the pump beam B incident on the semiconductor device D as an inspection target is adjusted, the detection sensitivity of the electromagnetic wave from the semiconductor device D is improved in many cases.

It is preferable that the reference value for performing the correction is 0.5% relative to the maximum value of the reference device, since the difference between the maximum values of the amplitude waveform of the electromagnetic wave is 0.5% or less upon successively measuring the same portion under the same condition. At this time, the reference value for performing the correction is not limited thereto, but may be modified in accordance with the inspection target, since the reference value differs depending on functions of the semiconductor device D.

When the difference between the maximum values of the amplitude waveform of the electromagnetic wave is equal to or less than the reference value in the step (S14) of correcting the sensitivity, the process proceeds to a step (S15) of inspecting a predetermined inspection position in the semiconductor device D as an inspection target, and the amplitude waveform of the electromagnetic wave generated from the inspection position is stored as shown in FIG. 6B.

Subsequently, in a determination step (S16), a value V00 (FIG. 6A) of the amplitude waveform of the electromagnetic wave at time t5 of the amplitude waveform of the electromagnetic wave generated from the inspection position of the reference device is compared to a value V101 (FIG. 6B) of the amplitude waveform of the electromagnetic wave generated from the semiconductor device D as an inspection target. Then, when the difference therebetween is equal to or less than the reference value for performing the step (S14) of correcting the sensitivity, the semiconductor device D as an inspection target is determined to be a non-defective device. Alternatively, when the difference therebetween is equal to or more than the reference value, the semiconductor device D as an inspection target is determined to be a defective device.

With such a configuration, it is possible to correct the sensitivity so as to be equal to the device sensitivity when the reference device is measured, by configuring the structure provided in the semiconductor device D to easily generate the electromagnetic wave as a source for generating the amplitude waveform of the electromagnetic wave when irradiating the pulse laser beam. Accordingly, it is possible to prevent an erroneous determination for the difference in the inspection result which be caused due to a difference in the device sensitivity when the reference device and the inspection device are measured.

The structure A used in the inspection unit according to the invention in FIG. 1 is arranged on the periphery of the board 3. The location of the structure A arranged is not limited to the periphery of the board 3, but may be arranged in any part of the board 3 without departing from the scope of the invention.

Figure 7:
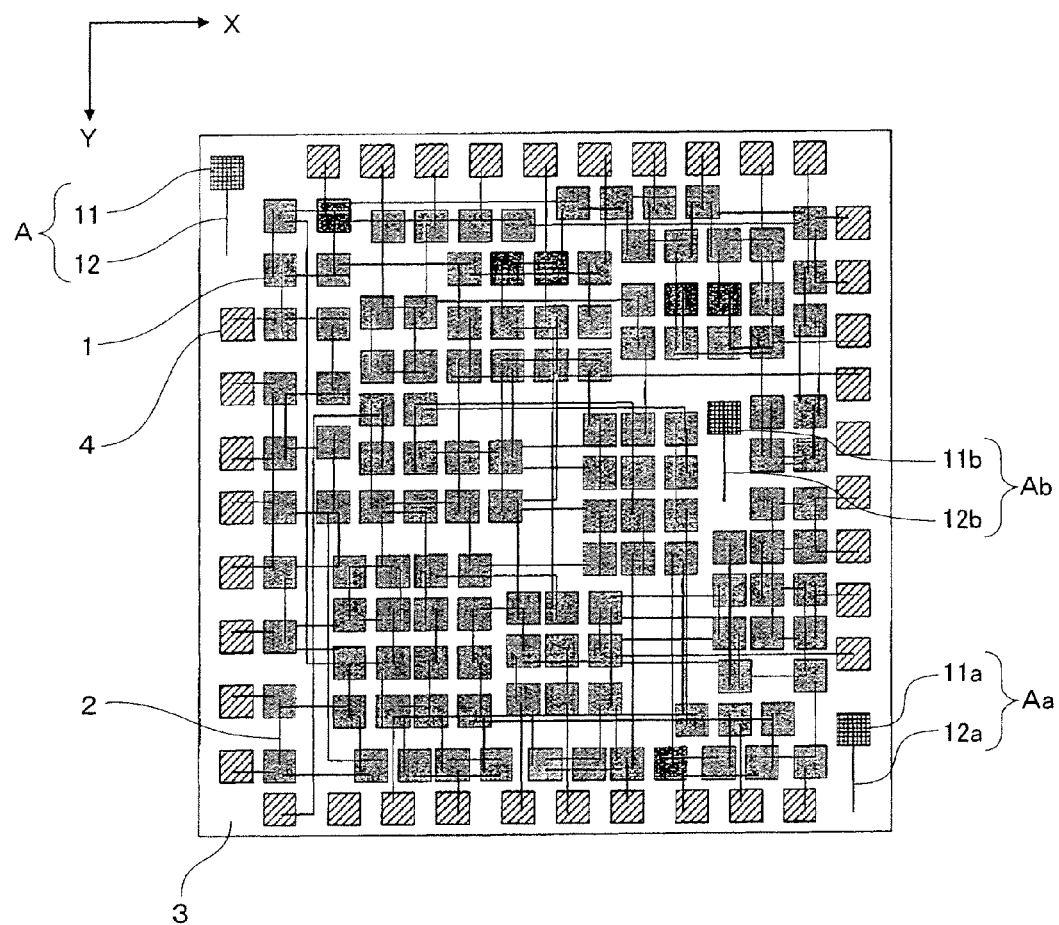
FIG. 7 is a diagram illustrating another circuit configuration of the semiconductor device according to the first embodiment of the invention.

In FIG. 1 used to describe the first embodiment, the structure A included in the semiconductor device is just one. However, a structure Aa which has the same structure as the structure A in a semiconductor device shown in FIG. 7 and includes a diffusion region 11a and a wiring line 12a, a structure Ab which has the same structure as the structure Aa and includes a diffusion region 11b and a wiring line 12b, and the like may be plurally arranged on the board 3. At this time, when the electromagnetic wave is not radiated from the structure A for some reason such as a problem with a process of manufacturing the semiconductor device or an external load after the manufacturing process, the amplitude waveform of the electromagnetic wave generated from the structure Aa may be compared to the amplitude waveform of the electromagnetic wave generated from the structure Ab to correct the detection sensitivity of the electromagnetic wave.

Figure 8:
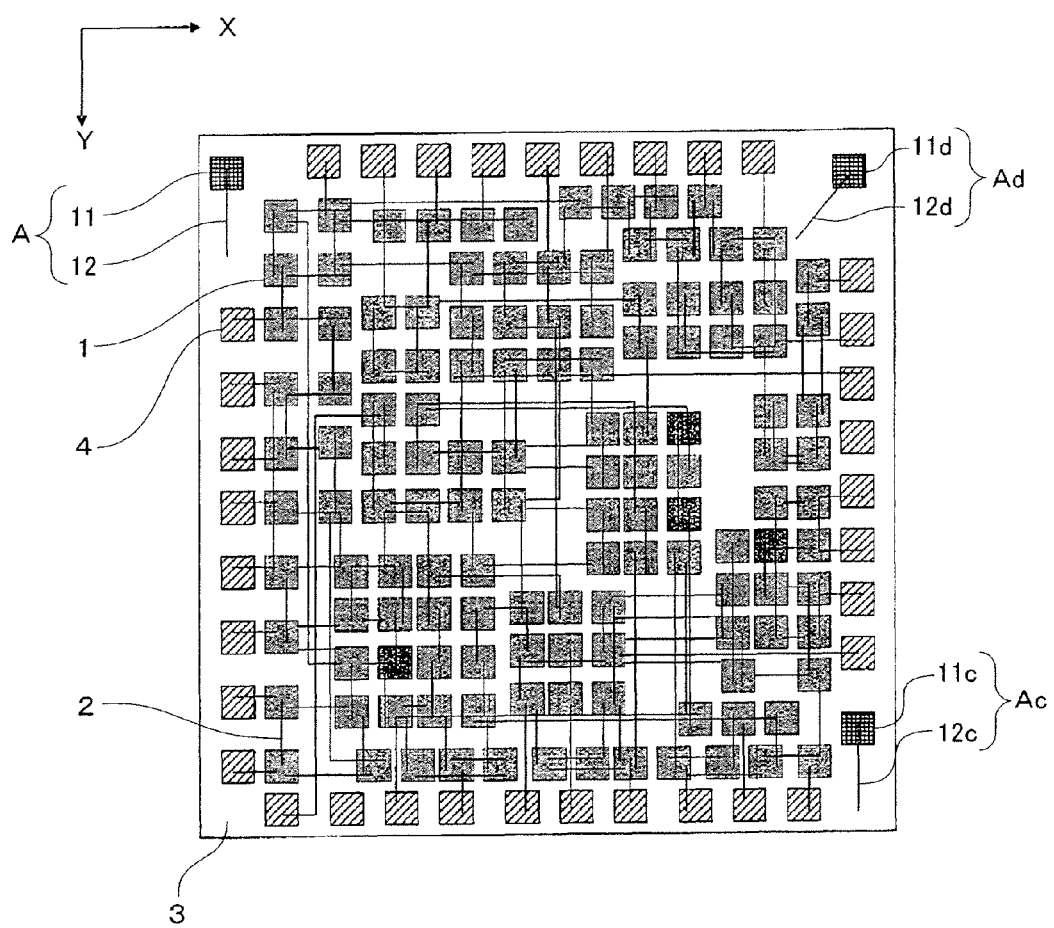
FIG. 8 is a diagram illustrating yet another circuit configuration of the semiconductor device according to the first embodiment of the invention.

When a structure which is the same as the structure A is arranged in the same semiconductor device as shown in FIG. 8, the wiring line 12 and a wiring line 12c connected to the diffusion region 11 and a diffusion region 11c, respectively, may not necessarily extend in the same direction (an X direction or a Y direction), and a structure Ac may be arranged so that the wirings extend in the X direction or the Y direction. Alternatively, when there is a space for arranging a wiring line, a wiring line 12d included in a structure Ad is not required to extend in the X direction or the Y direction, but may extend in any direction on an X-Y plane.

In illustration of the correction unit according to the first embodiment, the example in which the maximum value V0 of the amplitude waveform at the time T in FIG. 5A is detected to correct the sensitivity of the electromagnetic wave has been described. However, the amplitude magnitude of the electromagnetic wave at this time may not be used. The magnitude of the electromagnetic wave at any time, for example, a magnitude V4 of the amplitude of the electromagnetic wave at time T1 may be used to correct the detection sensitivity of the electromagnetic wave.

Second Embodiment

Figure 9:
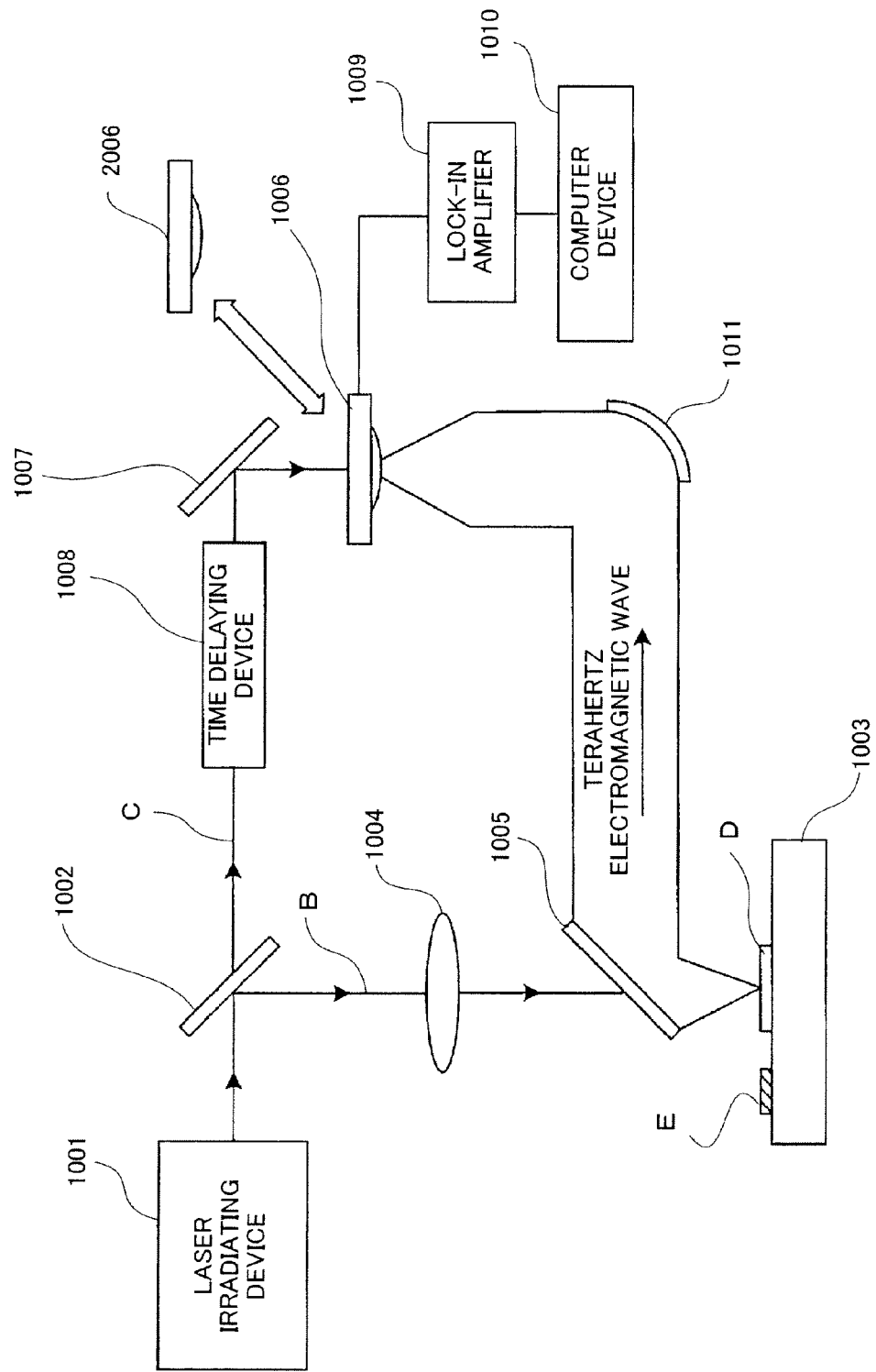
FIG. 9 is a block diagram illustrating an electromagnetic wave detector used in non-contact inspection according to a second embodiment of the invention.

FIG. 9 is a diagram for explaining a method of correcting detection sensitivity, according to a second embodiment, using a non-contact inspection device including a correcting semiconductor device when an electromagnetic wave detector is replaced. In FIG. 9, the same reference numerals are given to constituent elements having the same functions as those of the constituent elements described in FIG. 3 and the description thereof is omitted.

In the non-contact inspecting device shown in FIG. 9, a semiconductor device D having a structure A for easily radiating an electromagnetic wave is provided on a stage 1003. A pump beam B can be irradiated onto the semiconductor device D, by moving the stage 1003 in a horizontal direction or a vertical direction. Reference Numeral 2006 denotes a replacement electromagnetic wave detector.

Figure 10:
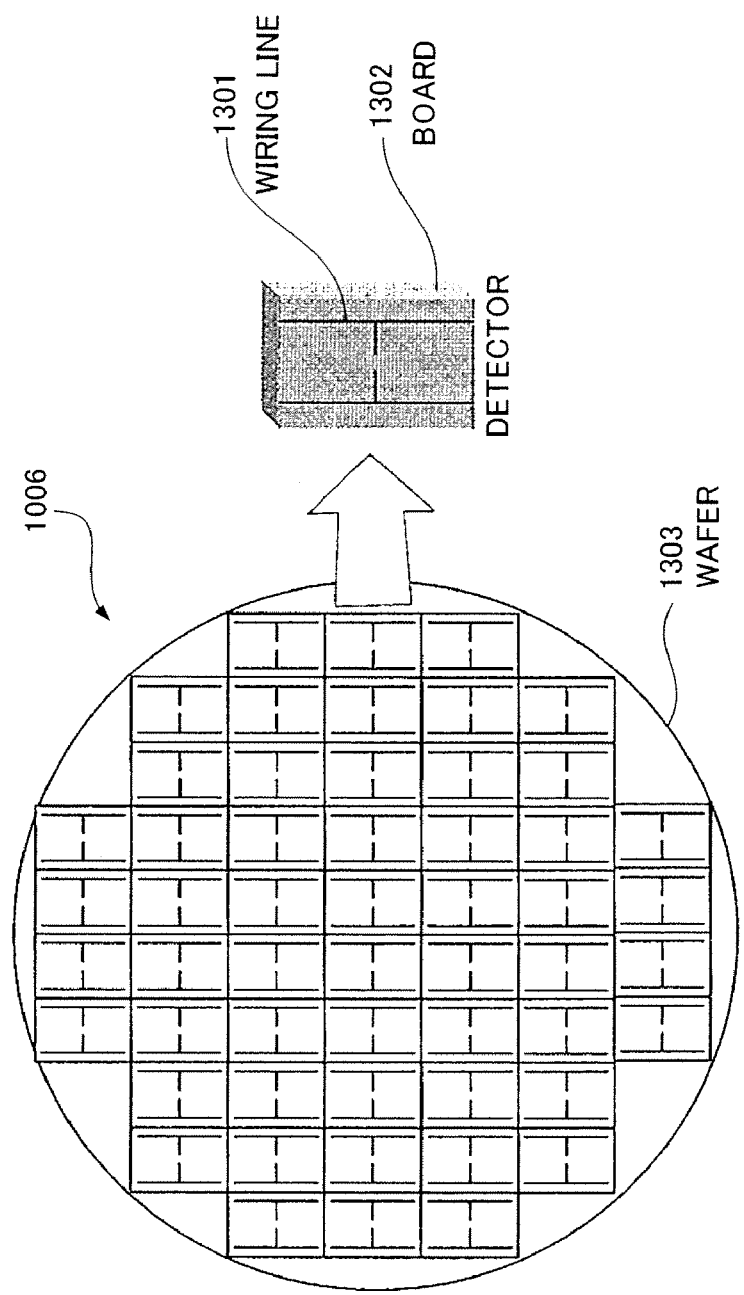
FIG. 10 is a diagram illustrating the configuration of the electromagnetic wave detector according to the second embodiment.

A configuration example of the electromagnetic wave detector 1006 which detects an amplitude waveform of an electromagnetic wave generated when a pulse laser beam is irradiated onto a predetermined position of the semiconductor device D is simply shown in FIG. 10.

The electromagnetic wave detector 1006 is manufactured by depositing and sputtering a wiring line 1301 on a board 1302. Actually, the plurality of detectors (the boards 1302 and the wiring lines 1301) are simultaneously manufactured on a wafer 1303 which becomes the board 1302, individually divided, and installed in holders, which is not shown in FIG. 9, of the electromagnetic wave detectors to be used.

In this case, there is a possibility that the electromagnetic wave detectors 1006 are not normally manufactured since the angle of a probe beam C incident on the electromagnetic wave detectors 2006 is changed after replacement of the electromagnetic wave detector 1006 or a problem may arise during a manufacturing process. Accordingly, it is necessary to adjust sensitivity in addition to confirming operations of the electromagnetic wave detector 1006.

Figure 11:
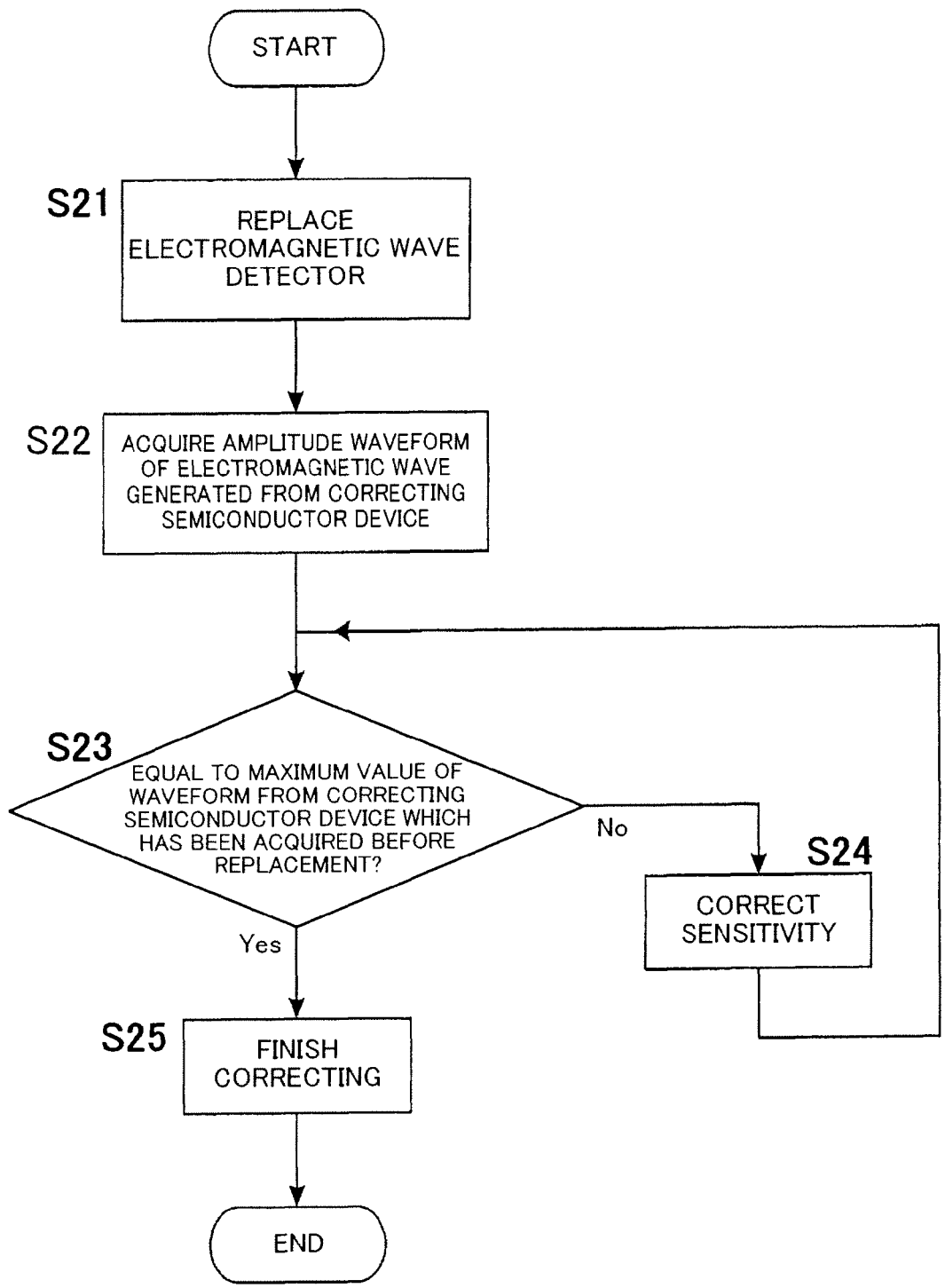
FIG. 11 is a flowchart illustrating a method of correcting the electromagnetic wave detector according to the second embodiment.

FIG. 11 is a flowchart showing a correcting step when the electromagnetic wave detector is replaced. Since a criterion for determining whether the sensitivity correcting step is necessary or a method of correcting the sensitivity are the same as those according to the first embodiment, when the electromagnetic wave detector 1006 is replaced, different details from those according to the first embodiment will be described.

In a step (S21) of replacing the electromagnetic wave detector, the electromagnetic wave detector 2006 is replaced with the electromagnetic wave detector 1006, installed in the holder (not shown) of the electromagnetic wave detector, and provided in the non-contact inspection device.

In a step (S22) of acquiring an amplitude waveform of an electromagnetic wave generated from a correcting semiconductor device E, the stage 1003 is operated so as to irradiate the pump beam B of the replaced electromagnetic wave detector 2006 onto a position of the structure A of the correcting semiconductor device E to acquire the amplitude waveform of the electromagnetic wave generated.

Figure 12:
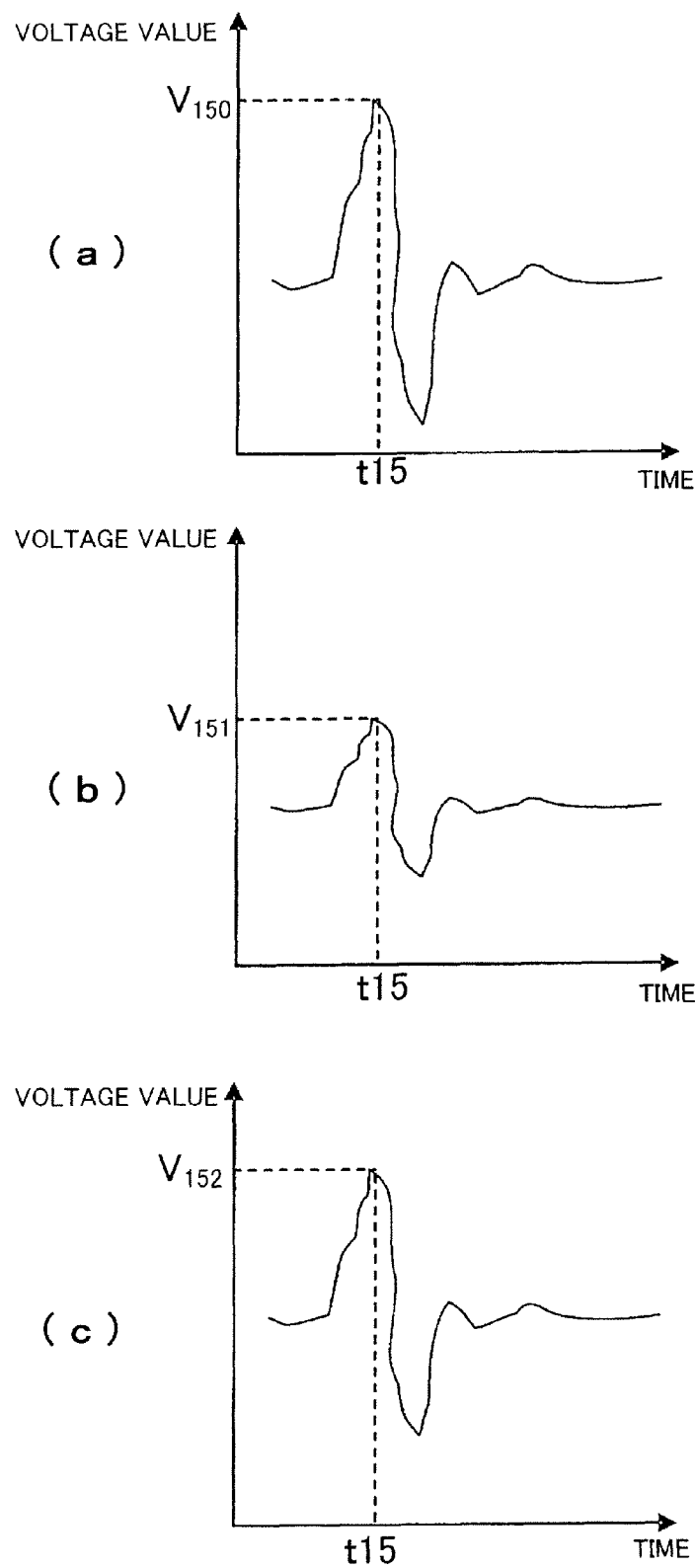
FIGS. 12A to 12C are diagrams illustrating amplitude waveforms of electromagnetic waves when irradiating a pulse laser beam to a structure A of a semiconductor device of correcting according to the second embodiment.

FIGS. 12A to 12C are schematic diagrams illustrating the amplitude waveforms of the electromagnetic waves when irradiating a pulse laser beam to the structure A of the correcting semiconductor device E. FIG. 12A shows the amplitude waveform of the electromagnetic wave generated from the electromagnetic wave detector 1006. FIG. 12B shows the amplitude waveform of the electromagnetic wave generated from the electromagnetic wave detector 2006. FIG. 12C shows the amplitude waveform of the electromagnetic wave generated from the electromagnetic wave detector 2006 after correction of the sensitivity.

In a step (S23) of determining whether the sensitivity correction of the electromagnetic wave detector 2006 is necessary, values V150 and V151 of the amplitude waveform of the electromagnetic wave at time T15 are compared to each other and whether the sensitivity correction is necessary is determined on the basis of the determination criterion described in the first embodiment. When the correction of the sensitivity is necessary, a step (S24) of correcting the sensitivity is performed by the method of correcting the sensitivity described in the first embodiment so that the amplitude value of the electromagnetic wave becomes V152.

After the correction of the sensitivity, the step (S23) of determining whether the sensitivity correction is necessary is performed again. When a difference between the maximum values is equal to or less than a reference value, the process finishes (S25).

With such a configuration, it is possible to correct variation in the maximum value of the amplitude waveform of the electromagnetic wave which are caused due to the replacement of the electromagnetic wave detector. Accordingly, since amplitude waveforms of electromagnetic waves acquired from different devices can be compared to each other, a database of the measured values can be made or an inspection criterion can be used between different devices, thereby improving the generality of a device.

In the second embodiment, when the difference in the maximum values is equal to or more than the reference value, the step (S24) of correcting the sensitivity is performed, and then the difference in the maximum values becomes the value equal to or less than the reference value. However, in some cases, the same sensitivity as that of the electromagnetic wave detector 1006 before the replacement may not be shown even though the step (S24) of correcting the sensitivity is performed several times due to the manufacturing defects of the replaced electromagnetic wave detector 2006. In this case, even though the difference between the maximum values is equal to or more than the reference value after the step S23 is performed several times, the step (S24) of correcting the sensitivity may not be performed but terminated. Then, another electromagnetic wave detector may be installed to perform steps of correcting and inspecting the sensitivity.

In the second embodiment, the correcting semiconductor device E is provided on the stage 1003. However, it is not necessary to provide the correcting semiconductor device E on the stage 1003 as long as the pump beam B can be irradiated and the amplitude waveform of the electromagnetic wave generated from the semiconductor device D can be detected by the electromagnetic wave detector 1006. In this case, the correcting semiconductor device E may be provided on any portion of the device.

The invention is not limited to the above-described embodiments, but may be modified in various forms without departing from the scope of the invention.

As described above, the method and the device for inspecting a semiconductor device according to the embodiments can improve inspection precision since the quality of a semiconductor device as an inspection target can be precisely determined without being influenced by a difference in measurement results caused due to insufficient sensitivity correction when acquiring the amplitude magnitude of the amplitude waveform of the electromagnetic wave. Moreover, the method and device are useful for preventing an erroneous quality determination when detecting a defect such as a broken wiring line in the semiconductor device where electronic circuits are formed on a board of an electronic element.

INDUSTRIAL APPLICABILITY

The invention contributes to improvement in quality control of various semiconductor devices since it is possible to precisely determine the quality of a semiconductor device as an inspection target.

The invention claimed is:

1. A method of inspecting a semiconductor device, comprising:
   an irradiation step of irradiating a pulse laser beam to any diffusion region in a semiconductor device as an inspection target, the semiconductor device being held in an non-bias state and including diffusion regions;
   a detection and conversion step of detecting an electromagnetic wave radiated from a laser beam irradiated position of the semiconductor device, and converting the detected electromagnetic wave into a time-varying voltage signal corresponding to a time waveform of an electric field amplitude of the electromagnetic wave; and
   a defect diagnosis step of detecting electric field distribution within the semiconductor device from the time-varying voltage signal to perform a defect diagnosis,
   the method further comprising:
   comparing a first time waveform of the electric field amplitude of the electromagnetic wave generated when irradiating the pulse laser beam to the diffusion region for correcting detection sensitivity of the electromagnetic wave which is provided in the semiconductor device as an inspection target and connected to at least one wiring line with a second time waveform of the electric field amplitude of the electromagnetic wave generated when irradiating the pulse laser beam to the diffusion region for correcting which is provided in a semiconductor device as a reference device;
   correcting detection sensitivity of the electromagnetic wave so that a maximum value of the amplitude magnitude of the electromagnetic wave for the first time waveform is equal to a maximum value of the amplitude magnitude of the electromagnetic wave for the second time waveform; and
   inspecting the semiconductor device as an inspection target.

2. The method according to claim 1, wherein the diffusion region for correcting the detection sensitivity of the electromagnetic wave is not electrically connected to the plurality of diffusion regions included in the semiconductor device.

3. The method according to claim 1, wherein the correction of the detection sensitivity of the electromagnetic wave is performed so that values of the amplitude magnitudes of the electromagnetic waves at a specific time are equal to each other in amplitude waveforms of the electromagnetic waves of the first time waveform and the second time waveform, instead of performing the correction using the maximum value of the amplitude magnitude of the electromagnetic wave.

4. A semiconductor device inspecting apparatus comprising:

an irradiation unit which two-dimensionally irradiates a pulse laser beam having a predetermined wavelength to a semiconductor device held in a non-bias state;

a detection and conversion unit which detects an electromagnetic wave radiated from a laser beam irradiated position of the semiconductor device and converts the detected electromagnetic wave into a time-varying voltage signal corresponding to a time waveform of an electric field amplitude of the electromagnetic wave;

a defect diagnosis unit which detects electric field distribution within the semiconductor device from the time-varying voltage signal to perform a defect diagnosis; and a semiconductor device for correcting sensitivity of the electromagnetic wave which is arranged within a range where the irradiation unit irradiate the pulse laser beam, wherein detection sensitivity of the electromagnetic wave generated when irradiating the pulse laser beam to the semiconductor device for correcting sensitivity of the electromagnetic wave before component replacement is equal to detection sensitivity of the electromagnetic wave generated after component replacement.

* * * * *